United States Patent [19]

Ondetti et al.

[11] Patent Number: 4,482,725

[45] Date of Patent: Nov. 13, 1984

[54] S-ACYLATION PRODUCTS OF MERCAPTOACYL AMINO ACIDS AND CARBOXYL GROUP CONTAINING DIURETICS

[75] Inventors: Miguel A. Ondetti; Denis E. Ryono, both of Princeton, N.J.

[73] Assignee: E. R. Squibb & Sons, Inc., Princeton, N.J.

[21] Appl. No.: 136,842

[22] Filed: Apr. 3, 1980

[51] Int. Cl.$^3$ .......................................... C07D 207/16
[52] U.S. Cl. .................................. 548/533; 424/266; 424/267; 424/274; 424/275; 424/285; 424/301; 546/208; 546/213; 546/214; 546/226; 548/344; 548/409; 548/495; 548/577; 549/72; 549/76; 549/494
[58] Field of Search ................. 260/326.12 A, 326.25, 260/326.35, 326.36, 326.43, 397.2, 455 R, 326.4, 326.42; 548/344, 533, 409, 495, 577; 549/72, 76, 494; 546/208, 213, 214, 226

[56] References Cited

U.S. PATENT DOCUMENTS

| | | | |
|---|---|---|---|
| 3,058,882 | 10/1962 | Stürm et al. | 424/263 |
| 3,255,241 | 12/1961 | Schultz et al. | 260/516 |
| 4,046,889 | 9/1979 | Ondetti et al. | 424/244 |
| 4,053,651 | 10/1977 | Ondetti et al. | 424/317 |
| 4,105,776 | 8/1978 | Ondetti et al. | 424/274 |
| 4,112,119 | 9/1978 | Ondetti et al. | 424/317 |
| 4,140,786 | 2/1979 | Ondetti et al. | 424/273 R |
| 4,140,797 | 2/1979 | Ondetti et al. | 424/319 |
| 4,154,840 | 5/1979 | Ondetti et al. | 424/267 |

FOREIGN PATENT DOCUMENTS

| | | |
|---|---|---|
| 861454 | 6/1978 | Belgium . |
| 873092 | 6/1979 | Belgium . |
| 2014132 | 8/1979 | United Kingdom . |

OTHER PUBLICATIONS

Derwent Abstract of Belgium Patent 879,159, published 2-1-80.
Bicking et al., J. Med. Chem., vol. 19, (1976), p. 530.
Bormann, Chemistry in Britain, vol. 15, (1979), p. 72.
Feit et al., J. Med. Chem., vol. 15, No. 1, (1972), p. 79.
Feit et al., J. Med. Chem., vol. 14, No. 5, (1971), p. 432.
Merkel et al., Eur. J. Med. Chem., vol. 11, (1976), p. 399.
Nielson et al., J. Med. Chem., vol. 18, No. 1, (1975), p. 41.
Thuillier et al., Eur. J. Med. Chem., vol. 9, (1974), p. 625.

Primary Examiner—Richard Raymond
Attorney, Agent, or Firm—Lawrence S. Levinson; Donald J. Barrack

[57] ABSTRACT

The S-acylation of a mercaptoacyl amino acid having ACE inhibitory action with a diuretic containing a carboxyl group yields a product having both ACE inhibitory action and diuretic activity in vivo.

5 Claims, No Drawings

S-ACYLATION PRODUCTS OF MERCAPTOACYL AMINO ACIDS AND CARBOXYL GROUP CONTAINING DIURETICS

BACKGROUND OF THE INVENTION

During the past few years a body of literature has developed around a type of compound known as ACE inhibitors; i.e., compounds which intervene in the angiotensinogen (renin)→angiotensin I→(ACE)→angiotensin II sequence by inhibiting angiotensin converting enzyme (ACE) and reducing or eliminating the formation of the pressor substance angiotensin II. These compounds can be described generally as mercaptoacyl amino acids. Exemplary references describing these compounds are set forth, infra., under the heading "Detailed Description of the Invention".

The most well known of the mercaptoacyl amino acid ACE inhibitors is captopril, the chemical name of which is (S)-1-(3-mercapto-2-methyl-1-oxopropyl)-L-proline. Belgian Pat. No. 873,092 published June 27, 1979 describes pharmaceutical compositions comprising captopril in combination with a variety of diuretics.

Bicking et al., J. Med. Chem., 19:530 (1976) discuss the formation of adducts from (diacylvinylaryloxy)acetic acids and mercaptoacetic acid. These adducts, like the parent compounds, are said to have diuretic activity. Further discussion of these adducts can be found in an article by Bormann in Chemistry in Britain, 15:72 (1979). The author suggests that the adducts function as prodrugs.

RELATED APPLICATION

U.S. patent application Ser. No. 90,820, filed Nov. 2, 1979 by Rudiger D. Haugwitz discloses adducts of mercaptoacyl amino acids having ACE inhibitory action and an α,β-unsaturated ketone having diuretic activity. The adducts exhibit both ACE inhibitory action and diuretic activity in vivo.

BRIEF DESCRIPTION OF THE INVENTION

The S-acylation of a mercaptoacyl amino acid having ACE inhibitory action with a diuretic containing a carboxyl group yields a product having both ACE inhibitory action and diuretic activity in vivo.

The preferred compounds of this invention have the formula

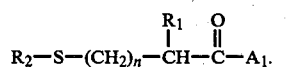

In formula I, and throughout the specification, the symbols are as defined below.

$R_1$ is hydrogen, alkyl, phenylalkyl, trifluoromethyl, or pentafluoroethyl;

$R_2$ is 5-(aminosulfonyl)-4-chloro-2-[(2-furanylmethyl)amino]benzoyl, 5-(aminosulfonyl)-2-[(2-furanylmethyl)amino]-4-(phenyloxy)benzoyl, 3-(aminosulfonyl)-5-(butylamino)-4-(phenyloxy)benzoyl, 5-(aminosulfonyl)-4-(phenyloxy)-3-(1-pyrrolidinyl)benzoyl, 5-(aminosulfonyl)-4-(benzoyl)-3-[[(3-thienyl)methyl]oxy]benzoyl, [2,3-dichloro-4-(2-methylene-1-oxobutyl)phenyloxy]acetyl, [[4-(2,2-diacetylvinyl)-2,3-dichlorophenyl]oxy]acetyl, or [[2,3-dichloro-4-(2-thienylcarbonyl)phenyl]oxy]acetyl;

$A_1$ is an α-amino or α-imino acid residue, or ester thereof, joined to the adjacent carbonyl group to form an amide linkage; and n is 1 or 2.

The term "alkyl", as used throughout the specification, refers to groups having 1 to 7 carbon atoms. Alkyl groups having 1, 2 or 3 carbon atoms are preferred.

The α-amino and α-imino acid residues represented by $A_1$ can be either naturally occurring or synthetic. Exemplary groups are residues of L-proline, 4-hydroxy-L-proline, 4-chloro-L-proline, 4-fluoro-L-proline, 4,4-difluoro-L-proline, 4,4-ethylenedioxy-L-proline, 4,4-ethylenedithio-L-proline, 4-phenylthio-L-proline, 4-methoxy-L-proline, 4-methyl-L-proline, L-pipecolic acid, 5-hydroxy-L-pipecolic acid, L-4-thiazolidinecarboxylic acid, tryptophane, glycine, alanine, phenylalanine, leucine, N-methylleucine, isoleucine, valine, arginine, sarcosine, serine, aspargine, lysine, histidine, cysteine, methionine, threonine, glutamine, and tyrosine.

DETAILED DESCRIPTION OF THE INVENTION

The S-acylation of a mercaptoacyl amino acid having ACE inhibitory action with a diuretic containing a carboxyl group yields a product having both ACE inhibitory action and diuretic activity in vivo.

Exemplary of the mercaptoacyl amino acids having ACE inhibitory action contemplated for use as a starting material to prepare the compounds of this invention are those compounds having the formula

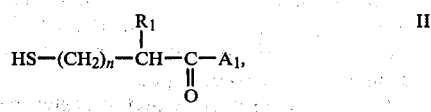

wherein the symbols $A_1$, $R_1$, and n have the meanings set forth above. Procedures for preparing the ACE inhibitors are disclosed in the patent literature.

U.S. Pat. Nos. 4,046,889, issued Sept. 6, 1979; 4,105,776, issued Aug. 8, 1978; and 4,154,840, issued May 15, 1979; describe compounds of formula II wherein $A_1$ is, inter alia, proline, hydroxyproline, pipecolic acid, or 5-hydroxypipecolic acid, or carboxylic acid esters thereof; and $R_1$ is hydrogen, alkyl or phenylalkyl.

U.S. Pat. Nos. 4,053,651 issued Oct. 11, 1977; 4,112,119, issued Sept. 5, 1978; 4,140,797, issued Feb. 20, 1979; and 4,140,786, issued Feb. 20, 1979; describe compounds of formula II wherein $A_1$ is, inter alia, alanine, leucine, phenylalanine, arginine, sarcosine, serine, asparagine, lysine, histidine, glycine, tryptophane, cysteine, methionine, N-methylleucine, valine, threonine, glutamine, tyrosine, N-benzylglycine or N-benzylglycine, and carboxylic acid esters thereof, and $R_1$ is hydrogen, alkyl or phenylalkyl.

U.S. Pat. No. 4,154,935, issued May 15, 1979 describes compounds of formula II wherein $R_1$ is hydrogen, alkyl or trifluoromethyl and $A_1$ is proline, 4-haloproline, 4,4-dihaloproline, 4-trifluoromethylproline, 5-halopipecolic acid, 5,5-dihalopipecolic acid, 5-trifluoromethylpipecolic acid or pipecolic acid, and carboxylic acid esters thereof.

U.S. Pat. Nos. 4,129,566, issued Dec. 12, 1978; and 4,154,942, issued May 15, 1979; describe compounds of formula II wherein $R_1$ is hydrogen or alkyl and $A_1$ is 3,4-dehydroproline or 4,5-dehydropiperidine-2-carboxylic acid and carboxylic acid esters thereof.

British patent specification No. 2,014,132 published Aug. 22, 1979, describes compounds of formula II wherein $R_1$ is trifluoromethyl or pentafluoroethyl and $A_1$ is proline, pipecolic acid, or thiazolidine-4-carboxylic acid, and carboxylic acid esters thereof.

Belgian Pat. No. 861,454, issued June 2, 1978, describes compounds of formula II wherein $R_1$ is hydrogen or alkyl and $A_1$ is, inter alia, thiazolidine-4-carboxylic acid, and carboxylic acid esters thereof.

Diuretics containing carboxyl group are well known in the art. To obtain the preferred compounds of this invention, i.e., the compounds of formula I, the following diuretics can be used as starting materials: furosemide (see, for example, U.S. Pat. No. 3,058,882), 5-(aminosulfonyl)-2-[(2-furanylmethyl)amino]-4-(phenyloxy)benzoic acid (see, for example, *J. Med. Chem.*, 15, 79 (1972), bumetanide (see, for example, *J. Med. Chem.*, 14, 432 (1971)), piretanide (see, for example *Eur. J. Med. Chem.*, 11,399 (1976)), 5-(aminosulfonyl)-4-(benzoyl)-3-[[3-thienyl-methyl]oxy]benzoic acid (see, for example, *J. Med. Chem.*, 18, 41 (1975)), ethacrynic acid (see, for example, U.S. Pat. No. 3,255,241), [[4-(2,2-diacetylvinyl)-2,3-dichlorophenyl-]oxy]acetic acid (see, for example, *J. Med. Chem.*, 19, 530 (1976)), and ticrynafen (see, for example, *Eur. J. Med. Chem.*, 9, 625 (1974)).

The S-acylation of a mercaptoacyl amino acid of formula II with a diuretic containing a carboxyl group can be accomplished by first activating the carboxyl group of the diuretic. Various means for activating the carboxyl group are known in the art; for example, an imidazolide derivative or a mixed anhydride derivative of the diuretic can be formed.

The chemically activated diuretic can be reacted with a mercaptoacyl amino acid (e.g., of formula II) to obtain the products of this invention. The reaction proceeds readily in the presence of an organic base, e.g., triethylamine.

The compounds of this invention are useful as hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen (renin)→angiotensin I→(ACE)-→angiotensin II sequence by inhibiting angiotensin converting enzyme and reducing or eliminating the formation of the pressor substance angiotensin II. Thus by the administration of a composition containing a compound of this invention, angiotensin dependent hypertension in the species of mammal suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention will also exhibit diuretic activity in vivo.

The compounds of this invention can be formulated for use in the reduction of blood pressure in compositions such as tablets, capsules or elixirs for oral administration or in sterile solutions of suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are specific embodiments of this invention.

EXAMPLE 1

(S)-1-[3-[[5-(Aminosulfonyl)-4-chloro-2-[(2-furanylmethyl)amino]benzoyl]thio]-2-methyl-1-oxopropyl]-L-proline To a solution of 4.3 g of furosemide in 80 ml of dry tetrahydrofuran is added 2.7 g of carbonyldiimidazole. The reaction is stirred under nitrogen for 2½ hours at room temperature. At the end of this time 1.8 ml of triethylamine is added followed by a solution of 2.8 g of (S)-1-(3-mercapto-2-methyl-1-oxopropyl)-L-proline in 50 ml of tetrahydrofuran added over a period of 10 minutes. After stirring for about 16 hours at room temperature, the reaction mixture is diluted with 200 ml of ethyl acetate and rinsed with two 50 ml portions of 10% aqueous KHSO4, 50 ml of water and brine. The organic solution is dried Na2SO4 and concentrated in vacuo to yield 7.3 g of a glassy solid. Chromatography on 1 kg of silica gel using 20:5:2:1, chloroform:ethyl acetate:methanol:acetic acid, yield 4.0 g of partially purified material. The partially purified material (2.0 g) is passed through about 600 ml of LH-20, packed and eluted with 1:2 water:methanol. By taking 5 ml fractions at a flow rate of 1 ml/minute, 1.4 g of product is obtained after removal of solvents in vacuo.

EXAMPLES 2–9

Following the procedure of Example 1, but substituting the compound listed in column I for (S)-1-(3-mercapto-2-methyl-1-oxopropyl)-L-proline and the compound listed in column II for furosemide, yields the product listed in column III.

| | Column I | Column II | Column III |
| --- | --- | --- | --- |
| 2. | (S)—1-[3-mercapto-1-oxo-2-(trifluoromethyl)propyl]-L-proline | 5-(aminosulfonyl)-2-[(2-furanyl-methyl)amino]-4-(phenyloxy)benzoic acid | (S)—1-[3-[[5-(aminosulfonyl)-2-[(2-furanylmethyl)amino]-4-(phenyloxy)benzoyl]thio]-1-oxo-2-(trifluoromethyl)propyl]-L-proline |
| 3. | (S)—1-(3-mercapto-2-methyl-1-oxopropyl)-4-hydroxy-L-proline | bumetanide | (S)—1-[3-[[3-(aminosulfonyl)-5-(butylamino)-4-phenoxybenzoyl]-thio-2-methyl-1-oxopropyl]-4- |

-continued

| | Column I | Column II | Column III |
|---|---|---|---|
| 4. | (S)—1-(3-mercapto-2-methyl-1-oxopropyl)-4-chloro-L-proline | piretanide | hydroxy-L-proline (S)—1-[3-[[3-(aminosulfonyl)-4-phenoxy-5-(1-piperidinyl)-benzoyl]thio]-2-methyl-1-oxopropyl]-4-chloro-L-proline |
| 5. | (S)—1-[3-mercapto-oxo-2-(phenylmethyl)propyl]-4,4-difluoro-L-proline | 5-(aminosulfonyl)-4-(benzoyl)-3-[[(3-thienyl)methyl]oxy]benzoic acid | (S)—1-[3-[[5-(aminosulfonyl)-4-benzoyl-5-[(3-thienylmethyl)oxy]-benzoyl]thio]-2-methyl-1-oxopropyl]-4,4-difluoro-L-proline |
| 6. | (S)—1-(3-mercapto-2-methyl-oxopropyl)-4,4-ethylenedioxy-L-propline | ethacrynic acid | (S)—1-[3-[[[2,3-dichloro-4-(2-methylene-1-oxobutyl)phenoxy]-acetyl]thio]-2-methyl-1-oxopropyl]-4,4-ethylenedioxy-L-proline |
| 7. | (S)—1-(3-mercapto-2-methyl-1-oxopropyl)-4-phenylthio-L-proline | [[4-(2,2-diacetylvinyl)-2,3-dichlorophenyl]oxy]acetic acid | (S)—1-[3-[[[4-(2,2-diacetyl-vinyl)-2,3-dichlorophenoxy]-acetyl]thio]-2-methyl-1-oxopropyl]4-(phenylthio)-L-proline |
| 8. | (S)—1-(3-mercapto-2-methyl-oxopropyl)-4-methoxy-L-proline | ticrynafen | (S)—1-[3-[[[2,3-dichloro-4-(2-thienylcarbonyl)phenoxy]-acetyl]thio]-2-methyl-1-oxopropyl]-4-methoxy-L-proline |
| 9. | (S)—1-(3-mercapto-2-methyl-1-oxopropyl)-L-4-thiazolidinecarboxylic acid | furosemide | (S)—3-[3-[[3-(aminosulfonyl)-4-chloro-5-[(2-furanylmethyl)-amino]benzoyl]thio]-2-methyl-1-oxopropyl]-L-4-thiazolidinecarboxylic acid |

What is claimed is:

1. A compound having the formula

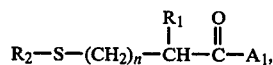

$$R_2-S-(CH_2)_n-\overset{R_1}{\underset{|}{CH}}-\overset{O}{\underset{\|}{C}}-A_1,$$

wherein $R_1$ is hydrogen, alkyl, phenylalkyl, trifluoromethyl, or pentafluoroethyl;

$R_2$ is 5-(aminosulfonyl)-4-chloro-2-[(2-furanylmethyl)amino]benzoyl, 5-(aminosulfonyl)-2-[(2-furanylmethyl)amino]-4-(phenyloxy)benzoyl, 3-(aminosulfonyl)-5-(butylamino)-4-(phenyloxy)benzoyl, 5-(aminosulfonyl)-4-(phenyloxy)-3-(1-pyrrolidinyl)-benzoyl, 5-(aminosulfonyl)-4-(benzoyl)-3-[[(3-thienyl)methyl]oxy]benzoyl, [2,3-dichloro-4-(2-methylene-1-oxobutyl)phenyloxy]acetyl, [[4-(2,2-diacetylvinyl)-2,3-dichlorophenyl]oxy]acetyl, or [[2,3-dichloro-4-(2-thienylcarbonyl)phenyl]oxy]acetyl;

$A_1$ is an α-amino or α-imino acid residue, or ester thereof, joined to the adjacent carbonyl group to form an amide linkage; and n is 1 or 2.

2. A compound in accordance with claim 1 wherein $A_1$ is L-proline, 4-hydroxy-L-proline, 4-chloro-L-proline, 4-fluoro-L-proline, 4,4-difluoro-L-proline, 4,4-ethylenedioxy-L-proline, 4,4-ethylenedithio-L-proline, 4-phenylthio-L-proline, 4-methoxy-L-proline, 4-methyl-L-proline, L-pipecolic acid, 5-hydroxy-L-pipecolic acid, L-4-thiazolidinecarboxylic acid, tryptophane, glycine, alanine, phenylalanine, leucine, N-methylleucine, isoleucine, valine, arginine, sarcosine, serine, aspargine, lysine, histidine, cysteine, methionine, threonine, glutamine, asnd tyrosine.

3. A compound in accordance with claim 1 wherein $R_1$ is methyl and n is 1.

4. A compound in accordance with claim 1 wherein $R_2$ is 5-(aminosulfonyl)-4-chloro-2-[(2-furanylmethyl)amino]benzoyl.

5. The compound in accordance with claim 1 (S)-1-[3-[[5-(aminosulfonyl)-4-chloro-2-[(2-furanylmethyl)amino]benzoyl]thio]-2-methyl-1-oxopropyl]-L-proline.

* * * * *